(12) United States Patent
Sasao et al.

(10) Patent No.: US 8,088,178 B2
(45) Date of Patent: Jan. 3, 2012

(54) HAIR COSMETIC COMPOSITION

(75) Inventors: Yuki Sasao, Aichi-ken (JP); Yasue Yamazaki, Aichi-ken (JP)

(73) Assignee: Hoyu Co., Ltd., Aichi-Ken (JP)

( * ) Notice: Subject to any disclaimer, the term of this patent is extended or adjusted under 35 U.S.C. 154(b) by 0 days.

(21) Appl. No.: 13/131,449

(22) PCT Filed: May 28, 2010

(86) PCT No.: PCT/JP2010/059079
§ 371 (c)(1),
(2), (4) Date: May 26, 2011

(87) PCT Pub. No.: WO2010/140543
PCT Pub. Date: Dec. 9, 2010

(65) Prior Publication Data
US 2011/0236329 A1    Sep. 29, 2011

(30) Foreign Application Priority Data
Jun. 1, 2009   (JP) .................................. 2009-132587

(51) Int. Cl.
*A61Q 5/10*    (2006.01)

(52) U.S. Cl. .............. 8/405; 8/431; 8/435; 8/552; 8/580
(58) Field of Classification Search .............. 8/405, 431, 8/435, 552, 580
See application file for complete search history.

(56) References Cited

U.S. PATENT DOCUMENTS 6,036,730 A * 3/2000 Yoshida et al. .................. 8/406

FOREIGN PATENT DOCUMENTS

| | | |
|---|---|---|
| JP | 2006-028107 A | 2/2006 |
| JP | 2007-077114 A | 3/2007 |
| JP | 2008-156252 A | 7/2008 |
| WO | 2008/096497 A1 | 8/2008 |

* cited by examiner

*Primary Examiner* — Eisa Elhilo
(74) *Attorney, Agent, or Firm* — Seager, Tufte & Wickhem LLC

(57) ABSTRACT

A hair cosmetic composition used for dyeing, bleaching, or destaining hair contains a fatty acid ester, a linear-chain higher fatty acid, polyethylene glycol having a number average molecular weight of 6,000 or more, an alkaline agent, and an oxidizing agent. The fatty acid ester is an ester of a fatty acid having a carbon number of 10 or less and an alcohol.

4 Claims, No Drawings

HAIR COSMETIC COMPOSITION

TECHNICAL FIELD

The present invention relates to a hair cosmetic composition used for dyeing, bleaching, or destaining hair.

BACKGROUND ART

Generally, a hair cosmetic composition used for dyeing, bleaching, or destaining hair contains an alkaline agent and an oxidizing agent. The oxidizing agent acts to remove melanin from hair. The alkaline agent acts to improve lightness of bleached hair by promoting the action of the oxidizing agent. When a hair cosmetic composition contains a dye, the alkaline agent also acts to improve the dyeability of hair by swelling hair so as to improve the permeability of the dye into the hair. Accordingly, lightness of the hair treated with a hair cosmetic composition can be improved by increasing the amounts of an alkaline agent and an oxidizing agent added to the hair cosmetic composition. Conventionally, ammonia and alkanolamine are commonly used as an alkaline agent in a hair cosmetic composition. However, a problem has been that pungent odor is produced when the amount of ammonia added is increased. Also, there has been a risk that, when the amount of alkanolamine added is increased, alkanolamine remaining on the hair after washing could cause irritation to the scalp.

Patent Document 1 discloses a hair bleach composition containing a water-soluble polymer compound, a higher alcohol, and an ester of a branched-chain fatty acid. The hair bleach composition of Patent Document 1 is intended to achieve both increasing lightness of the treated hair and reducing the production of pungent odor.

PRIOR ART DOCUMENTS

Patent Document 1: Japanese Laid-Open Patent Publication No. 2006-28107

SUMMARY OF INVENTION

Technical Problem to be Solved by the Invention

However, the hair bleach composition of Patent Document 1 does not sufficiently have a reducing effect on irritation to the scalp caused by an alkaline agent and an oxidizing agent. Further, because the application of the hair bleach composition to hair is difficult owing to its insufficient spreadability, in some cases the hair cannot be evenly bleached.

The present inventors have conducted intensive research. As a result, they have found that the aforementioned problems can be solved by using a specific oil component and a specific water-soluble polymer compound in combination, based on which the present invention was completed. An objective of the present invention is to reduce irritation to the skin caused by an alkaline agent and an oxidizing agent upon application of a hair cosmetic composition and to enable uniform dyeing, bleaching, or destaining of hair with the hair cosmetic composition.

Means for Solving the Problems

In order to achieve the aforementioned objective, and in accordance with one aspect of the present invention, a hair cosmetic composition used for dyeing, bleaching, or destaining hair is provided that contains a fatty acid ester, a linear-chain higher fatty acid, polyethylene glycol having a number average molecular weight of 6,000 or more, an alkaline agent, and an oxidizing agent. The fatty acid ester is an ester of a fatty acid having a carbon number of 10 or less and an alcohol.

The fatty acid ester used is preferably an ester of a fatty acid having a carbon number of 4 to 10 and an alcohol.

The number average molecular weight of polyethylene glycol used is preferably 10,000 or more.

The higher fatty acid used is preferably at least one selected from stearic acid, oleic acid, behenic acid, and palmitic acid.

EFFECTS OF THE INVENTION

According to the present invention, irritation to the skin caused by an alkaline agent and an oxidizing agent upon application of a hair cosmetic composition can be reduced, and hair can be evenly dyed, bleached, or destained with the hair cosmetic composition.

MODE FOR CARRYING OUT THE INVENTION

First Embodiment

Hereinbelow, a first embodiment, in which the present invention is embodied as a first, a second, and a third cosmetic composition used for bleaching or destaining hair, will be described.

(First Hair Cosmetic Composition)

The first hair cosmetic composition is a two-part type composed of a first and a second agent, which are mixed upon application, used for bleaching or destaining hair. The first agent contains a fatty acid ester, a higher fatty acid, polyethylene glycol, and an alkaline agent. The second agent contains an oxidizing agent.

(First Agent of First Hair Cosmetic Composition)

A fatty acid ester, a higher fatty acid, and polyethylene glycol contained in the first agent each act to improve the ease of application of the first hair cosmetic composition to hair when used in combination, which enables uniform bleaching or destaining of hair by the first hair cosmetic composition. The ease of application of the first hair cosmetic composition to hair is improved by the above components because a mixture of the first and second agents has good spreadability. A fatty acid ester also acts to improve lightness of the hair treated with the first hair cosmetic composition.

The fatty acid ester used is an ester of a fatty acid having a carbon number of 10 or less and an alcohol. When an ester of a fatty acid having a carbon number of 11 or more and an alcohol is used, the uniformity of bleaching or destaining of hair by the first hair cosmetic composition is impaired. From the viewpoint of improving the uniformity of bleaching or destaining of hair by the first hair cosmetic composition, an ester of a fatty acid having a carbon number of preferably 4 to 10, more preferably 6 to 10, and an alcohol is used. The alcohol residue of a fatty acid ester may be a residue of a compound in which one or more hydrogen atoms of aliphatic hydrocarbon are replaced by a hydroxyl group (OH) or a steroid alcohol (sterol) residue. Specific examples of the sterol include cholesterol, lanosterol, stigmasterol, sitosterol, fucosterol, campesterol, phytosterol, and ergosterol.

Specific examples of the ester of a fatty acid having a carbon number of 10 or less and an alcohol include diisopropyl adipate, diisobutyl adipate, dioctyl adipate, 2-hexyldecyl adipate, diisostearyl adipate, cetyl octanoate (a linear-chain fatty acid ester), cetyl 2-ethylhexanoate (a branched-chain fatty acid ester), cetyl isooctanoate, isononyl isononanoate, isodecyl isononanoate, isotridecyl isononanoate, diisopropyl sebacate, hexyldecyl dimethyloctanoate, acetylated lanolin, ethylene glycol di-2-ethylhexanoate, cetyl caprate, glyceryl tricaprate, and neopentyl glycol dicaprate. An ester of a fatty acid having a carbon number of 10 or less and pentaerythritol, and an ester of a fatty acid having a carbon number of 10 or less and dipentaerythritol can also be used. Alternatively, a fatty acid cholesteryl ester, which is an ester of a fatty acid having a carbon number of 10 or less and cholesterol, and a fatty acid lanosteryl ester, which is an ester of a fatty acid having a carbon number of 10 or less and lanosterol, can also be used. Among them, from the viewpoint of improving the uniformity of bleaching or destaining of hair by the first hair cosmetic composition, cetyl 2-ethylhexanoate, isononyl isononanoate, stearyl octanoate, and cholesteryl nonanoate are preferably used.

The content of a fatty acid ester in a mixture of the first and second agents is preferably 0.05 to 5% by mass, more preferably 0.25 to 2.5% by mass, and further preferably 0.5 to 1.5% by mass. When the content of a fatty acid ester is 0.05% by mass or more, the uniformity of bleaching or destaining of hair by the first hair cosmetic composition is improved. When the content of a fatty acid ester is 5% by mass or less, lightness of the hair treated with the first hair cosmetic composition is improved.

Higher fatty acid acts not only to improve the ease of application of the first hair cosmetic composition to hair but also to reduce irritation to the skin caused by an alkaline agent and an oxidizing agent, when used in combination with a fatty acid ester and polyethylene glycol. The higher fatty acid used is a linear-chain fatty acid without a branched chain. When a branched-chain fatty acid is used, irritation to the skin caused by an alkaline agent and an oxidizing cannot be reduced well. Any of a saturated fatty acid and an unsaturated fatty acid may be used as the higher fatty acid. Specific examples of the linear-chain higher fatty acid include lauric acid, myristic acid, palmitic acid, stearic acid, behenic acid, 12-hydroxystearic acid, and oleic acid. Among them, from the viewpoint of improving the uniformity of bleaching or destaining of hair by the first hair cosmetic composition, stearic acid, oleic acid, behenic acid, and palmitic acid are preferably used.

The content of a higher fatty acid in a mixture of the first and second agents is preferably 0.005 to 5% by mass, more preferably 0.025 to 2.5% by mass, and further preferably 0.05 to 1% by mass. When the higher fatty acid content is somewhere within the aforementioned ranges, irritation to the skin caused by an alkaline agent and an oxidizing agent is reduced well, and, in addition, the uniformity of bleaching or destaining of hair with the first hair cosmetic composition is improved.

Polyethylene glycol acts not only to improve the ease of application of the first hair cosmetic composition to hair but also to reduce irritation to the scalp caused by an alkaline agent and an oxidizing agent, when used in combination with a fatty acid ester and a higher fatty acid. The number average molecular weight of polyethylene glycol used must be 6,000 or more, and is preferably 10,000 or more, and more preferably 20,000 or more. When polyethylene glycol having a number average molecular weight of less than 6,000 is used, the uniformity of bleaching or destaining of hair by the first hair cosmetic composition is impaired. The upper limit of the number average molecular weight of polyethylene glycol used is preferably 5,000,000, although no particular limitation is imposed thereon. When polyethylene glycol having a number average molecular weight of 5,000,000 or less is used, the production cost of the first hair cosmetic composition is kept low.

The polyethylene glycol content in a mixture of the first and second agents is preferably 0.0005 to 5% by mass, more preferably 0.005 to 2.5% by mass, and further preferably 0.025 to 1% by mass. When the polyethylene glycol content is somewhere within the aforementioned ranges, the uniformity of bleaching or destaining of hair by the first hair cosmetic composition is improved.

An alkaline agent contained in the first agent acts to bleach or destain hair by promoting the action of an oxidizing agent contained in the second agent. Examples of the alkaline agent used include ammonia, alkanolamine, organic amine, inorganic alkali, a basic amino acid, and a salt of these substances. Specific examples of the alkanolamine include monoethanolamine and triethanolamine. Specific examples of the organic amine include 2-amino-2-methyl-1-propanol (AMP), 2-amino-2-methyl-1,3-propanediol, and guanidine. Specific examples of the inorganic alkali include sodium hydroxide, potassium hydroxide, sodium carbonate, and potassium carbonate. Specific examples of the basic amino acid include arginine and lysine. Specific examples of the salt include an ammonium salt. Only one kind of alkaline agent may be used, or two or more kinds thereof may be used in combination. When at least one of alkanolamine and ammonia is used as the alkaline agent, the effect of bleaching or destaining of hair by the first hair cosmetic composition is improved.

The alkaline agent is contained in the first agent in such an amount that the pH of the first agent is preferably within a range of 8 to 12. When the pH of the first agent is 8 or higher, the action of the oxidizing agent contained in the second agent is sufficiently promoted upon mixing of the first and second agents. When the pH of the first agent is 12 or lower, hair is less likely to be damaged by the first hair cosmetic composition.

The first agent may contain a component other than the aforementioned components, for example, water, a water-soluble polymer compound, an additional oil component, an additional polyhydric alcohol, a surfactant, sugar, a preservative, a stabilizing agent, a pH adjuster, a plant extract, a crude drug extract, a vitamin, a fragrance, an anti-oxidant, an ultraviolet ray-absorber, a chelating agent, and an oxidizing aid, as needed.

Water acts as, for example, a solvent.

As the water-soluble polymer compound, any of anionic, cationic, nonionic, and amphoteric ones may be used and any of natural compounds and synthetic compounds may be used. For example, hydroxyethyl cellulose, which is a nonionic synthetic polymer compound, may be used.

The oil component acts to moisturize hair. Specific examples of the oil component include oil/fat, wax, a higher alcohol, a hydrocarbon, an alkylglyceryl ether, an ester, and silicone.

Specific examples of the oil/fat include lanolin, olive oil, camellia oil, shea butter, almond oil, safflower oil, sunflower oil, soybean oil, cottonseed oil, sesame oil, corn oil, rapeseed oil, rice bran oil, rice germ oil, grape seed oil, avocado oil, macadamia nut oil, castor oil, coconut oil, and evening primrose oil. Specific examples of the wax include beeswax, candelilla wax, carnauba wax, jojoba oil, and lanolin. Specific examples of the higher alcohol include cetyl alcohol (cetanol), 2-hexyldecanol, stearyl alcohol, isostearyl alcohol, cetostearyl alcohol, oleyl alcohol, arachyl alcohol, behenyl alcohol, 2-octyldodecanol, lauryl alcohol, myristyl alcohol, decyltetradecanol, and lanolin alcohol.

Specific examples of the hydrocarbon include paraffin, an olefin oligomer, polyisobutene, hydrogenated polyisobutene, mineral oil, squalane, polybutene, polyethylene, microcrystalline wax, and petrolatum. Specific examples of the alkylglyceryl ether include batyl alcohol, chimyl alcohol, serachyl alcohol, and isostearyl glyceryl ether.

Specific examples of the ester include isopropyl myristate, octyldodecyl myristate, isopropyl palmitate, stearyl stearate, myristyl myristate, isotridecyl myristate, 2-ethylhexyl palmitate, octyldodecyl ricinoleate, a cholesteryl/lanosteryl ester of a fatty acid having a carbon number of 11 to 30, cetyl lactate, an ester of a fatty acid having a carbon number of 11 or more and pentaerythritol, an ester of a fatty acid having a carbon number of 11 or more and dipentaerythritol, diisostearyl malate, and dioctyl succinate.

Specific examples of the silicone include dimethylpolysiloxane (dimethicone), methylphenylpolysiloxane, decamethylcyclopentasiloxane, dodecamethylcyclohexasiloxane, terminal hydroxyl group-modified dimethylpolysiloxane, polyether-modified silicone, amino-modified silicone, betaine-modified silicone, alkyl-modified silicone, alkoxy-modified silicone, mercapto-modified silicone, carboxyl-modified silicone, and fluorine-modified silicone.

Only one kind of oil component may be used, or two or more kinds thereof may be used in combination.

Specific examples of the polyhydric alcohol include a glycol compound and a glycerin compound. Specific examples of the glycol compound include ethylene glycol, diethylene glycol, triethylene glycol, polyethylene glycol having a number average molecular weight of less than 10,000, propylene glycol, dipropylene glycol, and isoprene glycol. Specific examples of the glycerin compound include glycerin and polyglycerin.

The surfactant acts as an emulsifying agent or a solubilizing agent, and is used for adjusting the viscosity or improving the viscosity stability. As the surfactant, any of anionic, cationic, amphoteric, and nonionic surfactants may be used.

Specific examples of the anionic surfactant include alkyl ether sulfate, alkyl sulfate, alkenyl ether sulfate, alkenyl sulfate, olefin sulfonate, alkanesulfonate, a saturated or unsaturated fatty acid salt, alkyl or alkenyl ether carbonate, an α-sulfofatty acid salt, an N-acylamino acid type surfactant, a phosphate mono- or di-ester type surfactant, and a sulfosuccinate ester. A counterion for the anionic group of these surfactants may be, for example, any of a sodium ion, a potassium ion, and triethanolamine. For example, sodium lauryl sulfate, which is alkyl sulfate, may be used as the surfactant.

Specific examples of the cationic surfactant include laurylۗtrimethylammonium chloride, cetyltrimethylammonium chloride, stearyltrimethylammonium chloride, alkyltrimethylammonium chloride, distearyldimethylammonium chloride, cetyltrimethylammonium bromide, stearyltrimethylammonium bromide, lanolin fatty acid aminopropylethyldimethylammonium ethyl sulfate, stearyltrimethylammonium saccharin, cetyltrimethylammonium saccharin, methacryloyloxyethyltrimethylammonium chloride, and behenyltrimethylammonium methyl sulfate.

Specific examples of the amphoteric surfactant include cocobetaine, lauramidopropyl betaine, cocamidopropyl betaine, sodium lauroamphoacetate, sodium cocoamphoacetate, and laurylbetaine (betaine lauryldimethylamino acetate).

Specific examples of the nonionic surfactant include an ether-type nonionic surfactant and an ester-type nonionic surfactant.

Specific examples of the ether-type nonionic surfactant include polyoxyethylene (hereinafter, referred to as POE) cetyl ether (Ceteth), POE stearyl ether (Steareth), POE behenyl ether, POE oleyl ether (Oleth), POE lauryl ether (Laureth), POE octyldodecyl ether, POE hexyldecyl ether, POE isostearyl ether, POE nonylphenyl ether, and POE octylphenyl ether.

Specific examples of the ester-type nonionic surfactant include POE sorbitan monooleate, POE sorbitan monostearate, POE sorbitan monopalmitate, POE sorbitan monolaurate, POE sorbitan trioleate, POE glyceryl monostearate, POE glyceryl monomyristate, POE sorbitol tetraoleate, POE sorbitol hexastearate, POE sorbitol monolaurate, POE sorbitol beeswax, polyethylene glycol monooleate, polyethylene glycol monostearate, polyethylene glycol monolaurate, lipophilic glyceryl monooleate, lipophilic glyceryl monostearate, self-emulsifying glyceryl monostearate, sorbitan monooleate, sorbitan sesquioleate, sorbitan trioleate, sorbitan monostearate, sorbitan monopalmitate, sorbitan monolaurate, a sucrose fatty acid ester, decaglyceryl monolaurate, decaglyceryl monostearate, decaglyceryl monooleate, and decaglyceryl monomyristate.

Only one kind of surfactant may be used, or two or more kinds thereof may be used in combination.

Specific examples of the sugar include sorbitol and maltose.

Specific examples of the preservative include paraben.

Specific examples of the stabilizer include phenacetin, 8-hydroxyquinoline, acetanilide, sodium pyrophosphate, barbituric acid, uric acid, and tannic acid.

Specific examples of the pH adjuster include lactic acid, levulinic acid, glycolic acid, tartaric acid, malic acid, pyrrolidone carboxylic acid (PCA), succinic acid, citric acid, glutamic acid, and arginine.

Specific examples of the antioxidant include ascorbic acid and sulfite.

Specific examples of the chelating agent include ethylenediaminetetraacetic acid (EDTA), diethylenetriaminepentaacetic acid and salts thereof, and hydroxyethanediphosphonic acid (HEDP) and salts thereof.

Specific examples of the oxidizing aid include persulfate such as ammonium persulfate, potassium persulfate, and sodium persulfate. An oxidizing aid is used to intensify bleaching or destaining of hair by the first hair cosmetic composition.

No particular limitation is imposed on the form of the first agent, and the first agent can be in the form of, for example, any of solid, liquid, gel, foam, and cream. Specific examples of the solid form include powder and a granule. Specific examples of the liquid form include an aqueous solution, a suspension, and an emulsified liquid. When the first agent is in the form of solid, the first agent may further contain a dispersant. Specific examples of the dispersant include a metallic salt of stearic acid such as calcium stearate and magnesium stearate, talc, crystalline cellulose, low-substituted hydroxypropyl cellulose, dextrin, and starch.

(Second Agent of First Hair Cosmetic Composition)

An oxidizing agent contained in the second agent acts to remove melanin from hair. Examples of the oxidizing agent used include hydrogen peroxide, urea peroxide, melamine peroxide, sodium percarbonate, potassium percarbonate, sodium perborate, potassium perborate, ammonium persulfate, sodium peroxide, potassium peroxide, magnesium peroxide, barium peroxide, calcium peroxide, strontium peroxide, a hydrogen peroxide adduct of sulfate, a hydrogen peroxide adduct of phosphate, and a hydrogen peroxide adduct of pyrophosphate.

The content of an oxidizing agent in the second agent is preferably 0.1 to 15.0% by mass, more preferably 2.0 to 9.0% by mass, and further preferably 3.0 to 6.0% by mass. When the oxidizing agent content is 0.1% by mass or more, melanin in hair is sufficiently removed. When the oxidizing agent content is 15.0% by mass or less, hair is less likely to be damaged by the first hair cosmetic composition.

When the second agent contains hydrogen peroxide as the oxidizing agent, a stabilizer improving the stability of hydrogen peroxide, for example, ethyleneglycol phenyl ether (phenoxyethanol), hydroxyethanediphosphonic acid, or a salt thereof is preferably added to the second agent. Specific examples of the hydroxyethanediphosphonate include tetrasodium hydroxyethanediphosphonate and disodium hydroxyethanediphosphonate.

The second agent may further contain a component that is generally contained in a composition used for bleaching or destaining hair as long as it does not block the action of each component of the second agent. For example, the second agent may contain a component that is contained in the aforementioned first agent but other than the alkaline agent.

No particular limitation is imposed on the form of the second agent, and the second agent can be in the form of, for example, any of solid (except for the case in which the oxidizing agent is liquid at a normal temperature), liquid, gel, foam, and cream. Specific examples of the solid form include powder and a granule. Specific examples of the liquid form include an emulsified liquid.

The first and second agents are used for bleaching or destaining hair by mixing both of the agents upon application and applying the necessary amount of the resulting mixture to hair using a comb or a brush.

(Second Hair Cosmetic Composition)

The second hair cosmetic composition is a three-part type composed of a first, a second, and a third agent, which are mixed upon application, used for bleaching or destaining hair.

The first agent of the second hair cosmetic composition has a formulation similar to that of the first agent of the first hair cosmetic composition except that it does not contain a fatty acid ester, a higher fatty acid, and polyethylene glycol, and contains at least an alkaline agent.

The second agent of the second hair cosmetic composition has the same formulation as the second agent of the first hair cosmetic composition, and contains at least an oxidizing agent.

The third agent of the second hair cosmetic composition has the same formulation as the first agent of the first hair cosmetic composition, and is in the form of powder or cream.

(Third Hair Cosmetic Composition)

The third hair cosmetic composition is a one-part type used for bleaching hair. The third hair cosmetic composition is contained in a container, for example an applicator container, and upon application, the composition is ejected from the container and applied to hair. The third hair cosmetic composition contains a fatty acid ester, a linear-chain higher fatty acid, polyethylene glycol having a number average molecular weight of 6,000 or more, an alkaline agent, and an oxidizing agent. The fatty acid ester is an ester of a fatty acid having a carbon number of 10 or less and an alcohol. The third hair cosmetic composition is in the form of powder; therefore, the alkaline agent and the oxidizing agent used are preferably in the form of powder. The third hair cosmetic composition may further contain a component that is generally contained in a composition used for bleaching hair as long as it does not block the action of each component of the third hair cosmetic composition.

According to the first embodiment, the following advantages can be attained.

A fatty acid ester, a higher fatty acid, and polyethylene glycol contained in the first, second, and third hair cosmetic compositions act to improve the ease of application of the hair cosmetic compositions to hair. Thus, by using any of the first, second, and third hair cosmetic compositions, hair can be evenly bleached or destained. Also, by using any of the first, second, and third hair cosmetic compositions, lightness of the treated hair can be improved, and also, irritation to the skin can be reduced.

When the fatty acid ester contained in each of the first, second, and third hair cosmetic compositions is an ester of a fatty acid having a carbon number of 4 to 10 and an alcohol, the uniformity of bleaching or destaining of hair by the hair cosmetic composition is improved.

When the number average molecular weight of polyethylene glycol contained in each of the first, second, and third hair cosmetic compositions is 10,000 or more, the uniformity of bleaching or destaining of hair by the hair cosmetic composition is improved.

The first embodiment may be modified as follows.

A fatty acid ester, a higher fatty acid, and polyethylene glycol may be contained in any of the agents that make up a multi-part type hair cosmetic composition. For example, although a fatty acid ester, a higher fatty acid, and polyethylene glycol are contained in the first agent of the first hair cosmetic composition, at least some of these components may be contained in the second agent of the first hair cosmetic composition, instead of the first agent. Also, although a fatty acid ester, a higher fatty acid, and polyethylene glycol are contained in the third agent of the second hair cosmetic composition, at least some of these components may be contained in the first or the second agent of the second hair cosmetic composition, instead of the third agent.

Each of the first, second, and third hair cosmetic compositions may be modified to a multi-part type composed of four or more agents.

Second Embodiment

Hereinbelow, a second embodiment, in which the present invention is embodied as a fourth hair cosmetic composition used for dyeing hair, will be described. The fourth hair cosmetic composition is a two-part type composed of a first and a second agent, which are mixed upon application.

The first agent of the fourth hair cosmetic composition contains a fatty acid ester, a linear-chain higher fatty acid, polyethylene glycol having a number average molecular weight of 6,000 or more, an alkaline agent, and an oxidizing agent. The fatty acid ester is an ester of a fatty acid having a carbon number of 10 or less and an alcohol. The second agent of the fourth hair cosmetic composition has the same formulation as the second agent of the first hair cosmetic composition, and contains at least an oxidizing agent.

The oxidation dye contained in the first agent can produce color as induced by oxidative polymerization by the oxidizing agent contained in the second agent. The oxidation dye contains at least a dye intermediate, and may additionally contain a coupler.

Specific examples of the dye intermediate include p-phenylenediamine, toluene-2,5-diamine (paratoluoylenediamine), N-phenyl-p-phenylenediamine, 4,4'-diaminodiphenylamine, p-aminophenol, o-aminophenol, p-methylaminophenol, N,N-bis(2-hydroxylethyl)-p-phenylenediamine, 2-hydroxyethyl-p-phenylenediamine, o-chlor-p-phenylenediamine, 4-amino-m-cresol, 2-amino-4-hydroxyethylamino anisole, 2,4-diaminophenol, and a salt of these substances. Only one kind of dye intermediate may be used, or two or more kinds thereof may be used in combination.

The coupler produces color by binding to the dye intermediate. Specific examples of the coupler include resorcine, 5-amino-o-cresol, m-aminophenol, α-naphthol, 5-(2-hydroxyethylamino)-2-methylphenol, m-phenylenediamine, 2,4-diaminophenoxyethanol, toluene-3,4-diamine, 2,6-diaminopyridine, diphenylamine, N,N-diethyl-m-aminophenol, phenylmethylpyrazolone, and a salt of these substances. Only one kind of coupler may be used, or two or more kinds thereof may be used in combination. An oxidation dye containing a dye intermediate and a coupler is preferably used since the dye is capable of changing the color tone of hair as desired.

The first agent of the fourth hair cosmetic composition may further contain, for example, at least one selected from oxidation dyes listed in "the Japanese Standards of Quasi-drug Ingredients" (published in June 2006, Yakuji Nippo Ltd.) and direct dyes.

No particular limitation is imposed on the form of the first and second agents, and they can be in the form of, for example, any of solid, liquid, gel, foam, and cream. Specific examples of the liquid form include an aqueous solution, a suspension, and an emulsified liquid. The first and second agents are used for dyeing hair by mixing both of the agents upon application and applying the necessary amount of the resulting mixture to hair using a comb or a brush.

According to the second embodiment, the following advantages can be attained.

A fatty acid ester, a higher fatty acid, and polyethylene glycol contained in the fourth hair cosmetic composition act to improve the ease of application of the fourth hair cosmetic composition to hair. Thus, by using the fourth hair cosmetic composition, hair can be evenly dyed. Also, by using the fourth hair cosmetic composition, lightness of the treated hair can be improved, and also, irritation to the skin can be reduced.

When the fatty acid ester contained in the fourth hair cosmetic composition is an ester of a fatty acid having a carbon number of 4 to 10 and an alcohol, the uniformity of dyeing of hair by the fourth hair cosmetic composition is improved.

When the number average molecular weight of the polyethylene glycol contained in the fourth hair cosmetic composition is 10,000 or more, the uniformity of dyeing of hair by the fourth hair cosmetic composition is improved.

The second embodiment may be modified as follows.

The fourth hair cosmetic composition may be modified to a three-part type similar to the second hair cosmetic composition or a one-part type similar to the third hair cosmetic composition. Alternatively, the fourth hair cosmetic composition may be modified to a multi-part type composed of four or more agents.

EXAMPLES

The hair dyes (hair cosmetic compositions) of Examples 1 to 25 and Comparative Examples 1 to 9 were prepared. Each of the hair dyes is a two-part type, in which the first agent has the formulation as shown in any of Tables 1 to 3, and the second agent has a common formulation as shown in Table 4. The unit of the content of each component of a hair dye as shown in Tables 1 to 4 is % by mass. The first and second agents of each of the hair dyes were mixed at a mass ratio of 1:1, and the resulting mixture was applied to a bundle of black human hair using a brush. The hair bundle was left at room temperature (25° C.) for 30 minutes, and then the hair dye adhering to the hair bundle was washed off with water. Furthermore, the hair bundle was shampooed twice and conditioned once. The hair bundle was blow-dried with warm air, and then left for a day. At this time, lightness, skin irritation, and level-dyeing properties were evaluated according to the method described below.

(Evaluation Method for Lightness)

Ten panelists were asked to visually observe the hair bundle dyed with each of the hair dyes under a standard light source, and score the lightness of the hair bundle on a 5-point scale, namely excellent (5 points), good (4 points), fair (3 points), slightly poor (2 points), and poor (1 point). The hair dye was rated as "excellent (5 points)", "good (4 points)", "fair (3 points)", "slightly poor (2 points)", or "poor (1 point)" when the average score was 4.6 or more, 3.6 or more and less than 4.6, 2.6 or more and less than 3.6, 1.6 or more and less than 2.6, and less than 1.6, respectively. The results of evaluation are shown in Tables 1 to 3.

(Evaluation Method for Skin Irritation)

Each of the hair dyes was applied on the upper arm of 10 panelists. Then, the hair dye was rated as "5", "4", "3", "2", or "1" when the number of panelists who responded that irritation was hardly felt after 10 minutes was 9 or more, 7 to 8, 5 to 6, 3 to 4, or 2 or less, out of 10, respectively. The results of evaluation are shown in Tables 1 to 3.

(Evaluation Method for Level-Dyeing Properties)

Ten panelists were asked to visually observe the hair bundle dyed with each of the hair dyes under a standard light source, and score the uniformity of color tone of hair bundle on a 5-point scale, namely excellent (5 points), good (4 points), fair (3 points), slightly poor (2 points), and poor (1 point). The hair dye was rated as "excellent (5 points)", "good (4 points)", "fair (3 points)", "slightly poor (2 points)", or "poor (1 point)" when the average score was 4.6 or more, 3.6 or more and less than 4.6, 2.6 or more and less than 3.6, 1.6 or more and less than 2.6, and less than 1.6, respectively. The results of evaluation are shown in Tables 1 to 3.

TABLE 1

| | Examples | | | | | | |
|---|---|---|---|---|---|---|---|
| Mixed components | 1 | 2 | 3 | 4 | 5 | 6 | 7 |
| Cetyl 2-ethylhexanoate | 2 | — | 2 | 2 | 2 | 2 | 2 |
| Isononyl isononanoate | — | 2 | — | — | — | — | — |
| Stearyl octanoate | — | — | — | — | — | — | — |
| Cholesteryl nonanoate | — | — | — | — | — | — | — |
| Stearic acid | 0.5 | 0.5 | — | 0.5 | 0.5 | 0.5 | 0.5 |
| Oleic acid | — | — | 0.5 | — | — | — | — |
| Palmitic acid | — | — | — | — | — | — | — |
| Behenic acid | — | — | — | — | — | — | — |
| Polyethylene glycol 6000 (molecular weight: 6,000) | — | — | — | 0.1 | — | — | — |

TABLE 1-continued

| | | | | | | | |
|---|---|---|---|---|---|---|---|
| Polyethylene glycol 10000 (molecular weight: 10,000) | — | — | — | — | 0.1 | — | — |
| Polyethylene glycol 20000 (molecular weight: 20,000) | — | — | — | — | — | 0.1 | — |
| Polyethylene glycol 35000 (molecular weight: 35,000) | — | — | — | — | — | — | 0.1 |
| Polyethylene glycol PEG-9M (molecular weight: 400,000) | — | — | — | — | — | — | — |
| Polyethylene glycol PEG-90M (molecular weight: 4,000,000) | 0.1 | 0.1 | 0.1 | — | — | — | — |
| Polyethylene glycol 4000 (molecular weight: 4,000) | — | — | — | — | — | — | — |
| Cetostearyl alcohol | 6 | 6 | 6 | 6 | 6 | 6 | 6 |
| POE(7)Cetyl ether | 2 | 2 | 2 | 2 | 2 | 2 | 2 |
| POE(10)Cetyl ether | 4 | 4 | 4 | 4 | 4 | 4 | 4 |
| POE(20)Cetyl ether | 3 | 3 | 3 | 3 | 3 | 3 | 3 |
| Stearyltrimethylammonium chloride | 0.3 | 0.3 | 0.3 | 0.3 | 0.3 | 0.3 | 0.3 |
| Hydroxyethyl cellulose | 0.3 | 0.3 | 0.3 | 0.3 | 0.3 | 0.3 | 0.3 |
| Glycerin | 2 | 2 | 2 | 2 | 2 | 2 | 2 |
| Light liquid isoparaffin | 2 | 2 | 2 | 2 | 2 | 2 | 2 |
| Sodium sulfite | 0.1 | 0.1 | 0.1 | 0.1 | 0.1 | 0.1 | 0.1 |
| Hydroxyethanediphosphonic acid | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 |
| L-Ascorbic acid | 0.3 | 0.3 | 0.3 | 0.3 | 0.3 | 0.3 | 0.3 |
| p-Phenylenediamine | 0.4 | 0.4 | 0.4 | 0.4 | 0.4 | 0.4 | 0.4 |
| p-Aminophenol | 0.6 | 0.6 | 0.6 | 0.6 | 0.6 | 0.6 | 0.6 |
| m-Aminophenol | 0.15 | 0.15 | 0.15 | 0.15 | 0.15 | 0.15 | 0.15 |
| 5-Amino-orthocresol | 0.15 | 0.15 | 0.15 | 0.15 | 0.15 | 0.15 | 0.15 |
| 2,4-Diaminophenoxyethanol | 0.05 | 0.05 | 0.05 | 0.05 | 0.05 | 0.05 | 0.05 |
| 28% Ammonia water | 5 | 5 | 5 | 5 | 5 | 5 | 5 |
| Monoethanolamine | 1 | 1 | 1 | 1 | 1 | 1 | 1 |
| Purified water | Balance | Balance | Balance | Balance | Balance | Balance | Balance |
| Total | 100 | 100 | 100 | 100 | 100 | 100 | 100 |
| Evaluation | | | | | | | |
| Lightness | 5 | 5 | 5 | 5 | 5 | 5 | 5 |
| Skin irritation | 5 | 5 | 5 | 5 | 5 | 5 | 5 |
| Level-dyeing properties | 5 | 5 | 5 | 3 | 4 | 5 | 5 |

| | Examples | | | | | |
|---|---|---|---|---|---|---|
| | 8 | 9 | 10 | 11 | 12 | 13 |
| Mixed components | | | | | | |
| Cetyl 2-ethylhexanoate | 2 | 2 | — | — | 2 | 2 |
| Isononyl isononanoate | — | — | — | — | — | — |
| Stearyl octanoate | — | — | 2 | — | — | — |
| Cholesteryl nonanoate | — | — | — | 2 | — | — |
| Stearic acid | 0.5 | 0.5 | 0.5 | 0.5 | — | — |
| Oleic acid | — | — | — | — | — | — |
| Palmitic acid | — | — | — | — | 0.5 | — |
| Behenic acid | — | — | — | — | — | 0.5 |
| Polyethylene glycol 6000 (molecular weight: 6,000) | — | — | — | — | — | — |
| Polyethylene glycol 10000 (molecular weight: 10,000) | — | — | — | — | — | — |
| Polyethylene glycol 20000 (molecular weight: 20,000) | — | — | — | — | — | — |
| Polyethylene glycol 35000 (molecular weight: 35,000) | — | — | — | — | — | — |
| Polyethylene glycol PEG-9M (molecular weight: 400,000) | 0.1 | — | — | — | — | — |
| Polyethylene glycol PEG-90M (molecular weight: 4,000,000) | — | 0.1 | 0.1 | 0.1 | 0.1 | 0.1 |
| Polyethylene glycol 4000 (molecular weight: 4,000) | — | 0.1 | — | — | — | — |
| Cetostearyl alcohol | 6 | 6 | 6 | 6 | 6 | 6 |
| POE(7)Cetyl ether | 2 | 2 | 2 | 2 | 2 | 2 |
| POE(10)Cetyl ether | 4 | 4 | 4 | 4 | 4 | 4 |
| POE(20)Cetyl ether | 3 | 3 | 3 | 3 | 3 | 3 |
| Stearyltrimethylammonium chloride | 0.3 | 0.3 | 0.3 | 0.3 | 0.3 | 0.3 |
| Hydroxyethyl cellulose | 0.3 | 0.3 | 0.3 | 0.3 | 0.3 | 0.3 |
| Glycerin | 2 | 2 | 2 | 2 | 2 | 2 |
| Light liquid isoparaffin | 2 | 2 | 2 | 2 | 2 | 2 |

TABLE 1-continued

| | | | | | | |
|---|---|---|---|---|---|---|
| Sodium sulfite | 0.1 | 0.1 | 0.1 | 0.1 | 0.1 | 0.1 |
| Hydroxyethanediphosphonic acid | 0.1 | 0.1 | 0.1 | 0.1 | 0.1 | 0.1 |
| Fragrance | 0.1 | 0.1 | 0.1 | 0.1 | 0.1 | 0.1 |
| L-Ascorbic acid | 0.3 | 0.3 | 0.3 | 0.3 | 0.3 | 0.3 |
| p-Phenylenediamine | 0.4 | 0.4 | 0.4 | 0.4 | 0.4 | 0.4 |
| p-Aminophenol | 0.6 | 0.6 | 0.6 | 0.6 | 0.6 | 0.6 |
| m-Aminophenol | 0.15 | 0.15 | 0.15 | 0.15 | 0.15 | 0.15 |
| 5-Amino-orthocresol | 0.15 | 0.15 | 0.15 | 0.15 | 0.15 | 0.15 |
| 2,4-Diaminophenoxyethanol | 0.05 | 0.05 | 0.05 | 0.05 | 0.05 | 0.05 |
| 28% Ammonia water | 5 | 5 | 5 | 5 | 5 | 5 |
| Monoethanolamine | 1 | 1 | 1 | 1 | 1 | 1 |
| Purified water | Balance | Balance | Balance | Balance | Balance | Balance |
| Total | 100 | 100 | 100 | 100 | 100 | 100 |
| Evaluation | | | | | | |
| Lightness | 5 | 5 | 4 | 4 | 5 | 5 |
| Skin irritation | 5 | 5 | 5 | 5 | 5 | 5 |
| Level-dyeing properties | 5 | 5 | 4 | 4 | 5 | 5 |

TABLE 2

| | Examples | | | | | | | | | | | |
|---|---|---|---|---|---|---|---|---|---|---|---|---|
| | 14 | 15 | 16 | 17 | 18 | 19 | 20 | 21 | 22 | 23 | 24 | 25 |
| Mixed components | | | | | | | | | | | | |
| Cetyl 2-ethylhexanoate | 0.5 | 1 | 3 | 5 | 2 | 2 | 2 | 2 | 2 | 2 | 2 | 2 |
| Stearic acid | 0.5 | 0.5 | 0.5 | 0.5 | 0.05 | 0.1 | 2 | 5 | 0.5 | 0.5 | 0.5 | 0.5 |
| Polyethylene glycol PEG-90M (molecular weight: 4,000,000) | 0.1 | 0.1 | 0.1 | 0.1 | 0.1 | 0.1 | 0.1 | 0.1 | 0.005 | 0.01 | 2 | 5 |
| Cetostearyl alcohol | 6 | 6 | 6 | 6 | 6 | 6 | 6 | 6 | 6 | 6 | 6 | 6 |
| POE(7)Cetyl ether | 2 | 2 | 2 | 2 | 2 | 2 | 2 | 2 | 2 | 2 | 2 | 2 |
| POE(10)Cetyl ether | 4 | 4 | 4 | 4 | 4 | 4 | 4 | 4 | 4 | 4 | 4 | 4 |
| POE(20)Cetyl ether | 3 | 3 | 3 | 3 | 3 | 3 | 3 | 3 | 3 | 3 | 3 | 3 |
| Stearyltrimethylammonium chloride | 0.3 | 0.3 | 0.3 | 0.3 | 0.3 | 0.3 | 0.3 | 0.3 | 0.3 | 0.3 | 0.3 | 0.3 |
| Hydroxyethyl cellulose | 0.3 | 0.3 | 0.3 | 0.3 | 0.3 | 0.3 | 0.3 | 0.3 | 0.3 | 0.3 | 0.3 | 0.3 |
| Glycerin | 2 | 2 | | 2 | 2 | 2 | 2 | 2 | 2 | 2 | 2 | 2 |
| Light liquid isoparaffin | 2 | 2 | 2 | 2 | 2 | 2 | 2 | 2 | 2 | 2 | 2 | 2 |
| Sodium sulfite | 0.1 | 0.1 | 0.1 | 0.1 | 0.1 | 0.1 | 0.1 | 0.1 | 0.1 | 0.1 | 0.1 | 0.1 |
| Hydroxyethanediphosphonic acid | 0.1 | 0.1 | 0.1 | 0.1 | 0.1 | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 | 0.1 | 0.1 | 0.1 | 0.1 | 0.1 |
| L-Ascorbic acid | 0.3 | 0.3 | 0.3 | 0.3 | 0.3 | 0.3 | 0.3 | 0.3 | 0.3 | 0.3 | 0.3 | 0.3 |
| p-Phenylenediamine | 0.4 | 0.4 | 0.4 | 0.4 | 0.4 | 0.4 | 0.4 | 0.4 | 0.4 | 0.4 | 0.4 | 0.4 |
| p-Aminophenol | 0.6 | 0.6 | 0.6 | 0.6 | 0.6 | 0.6 | 0.6 | 0.6 | 0.6 | 0.6 | 0.6 | 0.6 |
| m-Aminophenol | 0.15 | 0.15 | 0.15 | 0.15 | 0.15 | 0.15 | 0.15 | 0.15 | 0.15 | 0.15 | 0.15 | 0.15 |
| 5-Amino-orthocresol | 0.15 | 0.15 | 0.15 | 0.15 | 0.15 | 0.15 | 0.15 | 0.15 | 0.15 | 0.15 | 0.15 | 0.15 |
| 2,4-Diaminophenoxyethanol | 0.05 | 0.05 | 0.05 | 0.05 | 0.05 | 0.05 | 0.05 | 0.05 | 0.05 | 0.05 | 0.05 | 0.05 |
| 28% Ammonia water | 5 | 5 | 5 | 5 | 5 | 5 | 5 | 5 | 5 | 5 | 5 | 5 |
| Monoethanolamine | 1 | 1 | 1 | 1 | 1 | 1 | 1 | 1 | 1 | 1 | 1 | 1 |
| Purified water | Balance | Balance | Balance | Balance | Balance | Balance | Balance | Balance | Balance | Balance | Balance | Balance |
| Total | 100 | 100 | 100 | 100 | 100 | 100 | 100 | 100 | 100 | 100 | 100 | 100 |
| Evaluation | | | | | | | | | | | | |
| Lightness | 4 | 5 | 5 | 4 | 5 | 5 | 5 | 5 | 5 | 5 | 5 | 5 |
| Skin irritation | 5 | 5 | 5 | 5 | 4 | 5 | 5 | 4 | 5 | 5 | 5 | 5 |
| Level-dyeing properties | 4 | 5 | 5 | 5 | 4 | 5 | 5 | 4 | 3 | 4 | 5 | 4 |

TABLE 3

| | Comparative Examples | | | | | | | | |
|---|---|---|---|---|---|---|---|---|---|
| | 1 | 2 | 3 | 4 | 5 | 6 | 7 | 8 | 9 |
| Mixed components | | | | | | | | | |
| Cetyl 2-ethylhexanoate | — | — | — | — | — | — | 2 | 2 | 2 |
| Myristyl myristate | — | 2 | — | — | — | — | — | — | — |

TABLE 3-continued

|  | Comparative Examples | | | | | | | | |
|---|---|---|---|---|---|---|---|---|---|
|  | 1 | 2 | 3 | 4 | 5 | 6 | 7 | 8 | 9 |
| Isopropyl myristate | — | — | 2 | — | — | — | — | — | — |
| Octyldodecyl oleate | — | — | — | 2 | — | — | — | — | — |
| Isocetyl isostearate | — | — | — | — | 2 | — | — | — | — |
| Oleyl oleate | — | — | — | — | — | 2 | — | — | — |
| Stearic acid | 0.5 | 0.5 | — | 0.5 | — | 0.5 | — | — | 0.5 |
| Myristyl myristate | — | — | 0.5 | — | 0.5 | — | 0.5 | — | — |
| Isostearic acid | — | — | — | — | — | — | — | 0.5 | — |
| Polyethylene glycol PEG-90M (molecular weight: 4,000,000) | 0.1 | 0.1 | 0.1 | — | 0.1 | — | 0.1 | 0.1 | — |
| Polyethylene glycol 4000 (molecular weight: 4,000) | — | — | — | 0.1 | — | 0.1 | — | — | 0.1 |
| Cetostearyl alcohol | 6 | 6 | 6 | 6 | 6 | 6 | 6 | 6 | 6 |
| POE(7)Cetyl ether | 2 | 2 | 2 | 2 | 2 | 2 | 2 | 2 | 2 |
| POE(10)Cetyl ether | 4 | 4 | 4 | 4 | 4 | 4 | 4 | 4 | 4 |
| POE(20)Cetyl ether | 3 | 3 | 3 | 3 | 3 | 3 | 3 | 3 | 3 |
| Stearyltrimethylammonium chloride | 0.3 | 0.3 | 0.3 | 0.3 | 0.3 | 0.3 | 0.3 | 0.3 | 0.3 |
| Hydroxyethyl cellulose | 0.3 | 0.3 | 0.3 | 0.3 | 0.3 | 0.3 | 0.3 | 0.3 | 0.3 |
| Glycerin | 2 | 2 | 2 | 2 | 2 | 2 | 2 | 2 | 2 |
| Light liquid isoparaffin | 2 | 2 | 2 | 2 | 2 | 2 | 2 | 2 | 2 |
| Sodium sulfite | 0.1 | 0.1 | 0.1 | 0.1 | 0.1 | 0.1 | 0.1 | 0.1 | 0.1 |
| Hydroxyethanediphosphonic acid | 0.1 | 0.1 | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 | 0.1 | 0.1 |
| L-Ascorbic acid | 0.3 | 0.3 | 0.3 | 0.3 | 0.3 | 0.3 | 0.3 | 0.3 | 0.3 |
| p-Phenylenediamine | 0.4 | 0.4 | 0.4 | 0.4 | 0.4 | 0.4 | 0.4 | 0.4 | 0.4 |
| p-Aminophenol | 0.6 | 0.6 | 0.6 | 0.6 | 0.6 | 0.6 | 0.6 | 0.6 | 0.6 |
| m-Aminophenol | 0.15 | 0.15 | 0.15 | 0.15 | 0.15 | 0.15 | 0.15 | 0.15 | 0.15 |
| 5-Amino-orthocresol | 0.15 | 0.15 | 0.15 | 0.15 | 0.15 | 0.15 | 0.15 | 0.15 | 0.15 |
| 2,4-Diaminophenoxyethanol | 0.05 | 0.05 | 0.05 | 0.05 | 0.05 | 0.05 | 0.05 | 0.05 | 0.05 |
| 28% Ammonia water | 5 | 5 | 5 | 5 | 5 | 5 | 5 | 5 | 5 |
| Monoethanolamine | 1 | 1 | 1 | 1 | 1 | 1 | 1 | 1 | 1 |
| Purified water | Balance | Balance | Balance | Balance | Balance | Balance | Balance | Balance | Balance |
| Total | 100 | 100 | 100 | 100 | 100 | 100 | 100 | 100 | 100 |
| Evaluation | | | | | | | | | |
| Lightness | 1 | 2 | 2 | 2 | 2 | 2 | 4 | 3 | 4 |
| Skin irritation | 4 | 4 | 4 | 4 | 4 | 4 | 1 | 2 | 3 |
| Level-dyeing properties | 1 | 1 | 1 | 1 | 1 | 1 | 1 | 4 | 1 |

TABLE 4

| <Second agent> | |
|---|---|
| Components | |
| Cetanol | 3 |
| POE (30) Cetyl ether | 0.6 |
| POE (5,5) Cetyl ether | 0.2 |
| 35% Hydrogen peroxide water | 16.6 |
| Purified water | Balance |
| Total | 100 |

As shown in Tables 1 to 3, the hair dyes of Examples 1 to 25 were rated as "3" or higher in any of the evaluation items of lightness, skin irritation, and level-dyeing properties.

In contrast, the lightness and the level-dyeing properties of the hair dye of Comparative Example 1 lacking a fatty acid ester and the hair dyes of Comparative Examples 2 to 6 containing an ester of a fatty acid having a carbon number of 11 or more and an alcohol were evaluated lower than those of the hair dyes of Examples.

The skin irritation of the hair dye of Comparative Example 7 lacking a linear-chain higher fatty acid and the hair dye of Comparative Example 8 containing isostearic acid, which is a branched-chain higher fatty acid, instead of a linear-chain higher fatty acid was evaluated lower than that of the hair dyes of Examples.

The level-dyeing properties of the hair dye of Comparative Example 9 containing polyethylene glycol having a molecular weight of 4,000 was evaluated lower than that of the hair dyes of Examples.

The invention claimed is:

1. A hair cosmetic composition used for dyeing, bleaching, or destaining hair, comprising a fatty acid ester, a linear-chain higher fatty acid, polyethylene glycol having a number average molecular weight of 6,000 or more, an alkaline agent, and an oxidizing agent, the fatty acid ester being an ester of a fatty acid having a carbon number of 10 or less and an alcohol.

2. The hair cosmetic composition according to claim 1, wherein the fatty acid ester is an ester of a fatty acid having a carbon number of 4 to 10 and an alcohol.

3. The hair cosmetic composition according to claim 1, wherein the number average molecular weight of the polyethylene glycol is 10,000 or more.

4. The hair cosmetic composition according to claim 1, wherein the higher fatty acid is at least one selected from stearic acid, oleic acid, behenic acid, and palmitic acid.

* * * * *